United States Patent [19]

Takata et al.

[11] Patent Number: 5,218,146

[45] Date of Patent: Jun. 8, 1993

[54] PROCESS FOR PRODUCTION OF ACRYLIC ACID

[75] Inventors: Masahiro Takata, Himeji; Mamoru Takamura, Takasago; Shinichi Uchida, Himeji, all of Japan

[73] Assignee: Nippon Shokubai Kagaku Kogyo Co., Ltd., Osaka, Japan

[21] Appl. No.: 798,867

[22] Filed: Nov. 25, 1991

Related U.S. Application Data

[60] Continuation of Ser. No. 507,008, Apr. 10, 1990, abandoned, which is a division of Ser. No. 199,200, May 26, 1988, abandoned.

[30] Foreign Application Priority Data

May 27, 1987 [JP] Japan .................................. 62-127958

[51] Int. Cl.$^5$ ............................................. C07C 51/32
[52] U.S. Cl. .................................................... 562/535
[58] Field of Search ........................................ 562/535

[56] References Cited

U.S. PATENT DOCUMENTS

| | | | |
|---|---|---|---|
| 4,031,135 | 3/1977 | Engelbach et al. | 562/535 |
| 4,052,450 | 10/1977 | Krabetz et al. | 562/535 |
| 4,182,907 | 4/1980 | Grasselli et al. | 562/535 |
| 4,365,087 | 6/1982 | Kadowaki et al. | 562/535 |

FOREIGN PATENT DOCUMENTS

| | | | |
|---|---|---|---|
| 393670 | 7/1972 | Japan . | |
| 939713 | 10/1963 | United Kingdom | 562/535 |
| 996898 | 6/1964 | United Kingdom . | |
| 1034914 | 6/1967 | United Kingdom . | |
| 1036375 | 8/1967 | United Kingdom . | |
| 1220568 | 8/1969 | United Kingdom . | |
| 1390271 | 2/1972 | United Kingdom . | |
| 1450986 | 2/1974 | United Kingdom . | |

OTHER PUBLICATIONS

51-Petroleum, vol. 77 (1972) 37356m, Brit. 1,268,129.
23-Aliphatics, vol. 83 (1975) 9213t, U.S. 3, 859,346.
Chemical Abstracts, vol. 85 (1976) 126853d, Tr. Tallin Politekh, Inst. 1975, 530–060.
23-Aliphatics vol. 89 (1978) 163017n, Tr. Tallin. Politekh, Inta 1976, (405) 30–09.
Chemical Abstracts, vol. 89 (1978) 23780f, Japan. Kokai 77, 142,009.
23-Aliphatics vol. 93 (1980) 113905n Arm. Khim, Zh. 1980, 33(1) 18–22.
Vol. 97 (1982)–126992w, *Visn. L'viv. Politekh. Inst.* 1982, 163, 390–040.
23-Aliphatics, vol. 87 (1977) 5401q U.S. 4,016,185.
Chemical Abstracts vol. 96 (1982) 103581b *Afinidad* 1981 38(1975) 445-7.
Chemical Abstracts vol. 95 (1981) 80178p EP 25715.
Chemical Abstracts vol. 94 (1981) 16319n, Ger. Offen. 3,002,829.

*Primary Examiner*—Arthur C. Prescott
*Attorney, Agent, or Firm*—Burns, Doane, Swecker & Mathis

[57] ABSTRACT

A process for the production of acrylic acid by the two-stage catalytic vapor-phase oxidation of propylene with molecular oxygen, the first stage for oxidizing propylene to produce mainly acrolein and the second stage for oxidizing acrolein to produce mainly acrylic acid, which process comprises supplying to the first-stage reaction a raw gas containing a saturated aliphatic hydrocarbon having 1 to 5 carbon atoms in an amount in the range of 5 to 70% by volume, carbon dioxide in an amount in the range of 3 to 50% by volume, and the aliphatic hydrocarbon and the carbon dioxide in a total amount in the range of 20 to 80% by volume and further containing steam in an amount in the range of 0.5 to 8 mol per mol of propylene.

9 Claims, No Drawings

PROCESS FOR PRODUCTION OF ACRYLIC ACID

This application is a continuation of application Ser. No. 07/507,008, filed Apr. 10, 1990, now abandoned, which is a continuation of application Ser. No. 07/199,200, filed May 26, 1988, now abandoned.

BACKGROUND OF THE INVENTION

1. Field of the Invention

This invention relates to a process for the production of acrylic acid by the catalytic vapor-phase oxidation of propylene. More particularly, it relates to a process for highly efficient production of acrylic acid owing to the use of a raw gas of a specific composition.

2. Description of the Prior Art

The process for the production of acrylic acid by the two-stage (the first stage reaction for conversion of propylene mainly to acrolein and the second stage reaction for conversion of acrolein mainly to acrylic acid) catalytic vapor-phase oxidation of propylene has been known to the art. Any attempt at improving the productivity of this process in the formation of acrylic acid has been blamed for the following drawbacks: (1) The space velocity cannot be appreciably increased on account of the limit imposed on the quality of a catalyst (yield and service life) to be used. (2) The conversion of propylene cannot be enhanced without lowering the selectivity of the reaction for reaction products favoring the production aimed at. (3) The room for addition to the propylene content of the raw gas is limited because the removal of the heat of reaction and the protection of the reaction system against the danger of explosion pose themselves as serious problems.

In the circumstances, various studies have been made in search of a way of improving the productivity of a process employed for the production of acrylic acid. For example, a process which comprises recycling unaltered propylene for reuse thereby increasing the conversion of propylene is disclosed in G.B. Patent No. 996,898. Numerous publications regarding the reclamation of reaction off-gas leaving the reactor are found in literature. For example, U.S. Pat. No. 3,540,201 discloses a process which comprises varying the activity of a catalyst in two stages, increasing the activity continuously or gradually up to 100% from the entrance to the reaction tube along the length of the reaction tube, removing most of the condensible gas at the outlet of the second-stage reaction zone, and resupplying the reaction off-gas remaining after the removal of the condensible gas in the place of part or whole of steam to the first-stage reaction zone. This process entails a work of diluting the catalyst and consequently suffers from deficiency practicability. It also exhibits poor and hardly tolerable productivity because of the use of propylene at a low concentration.

U.S. Pat. No. 4,031,135 discloses a process which curbs the post-combustion by utilizing the returned off-gas. This returned off-gas substantially comprises nitrogen and additionally contains small amount of unaltered propylene, oxygen, propane, and carbon oxides.

G.B. Patent No. 1,450,986 discloses an invention which concerns use of carbon dioxide formed in a reaction system. The use of the carbon dioxide as the carrier gas is claimed to prevent the danger of explosion, facilitate the removal of the heat of reaction from the reaction bed, and contribute to heightening the yield. This patent, however, has no specific disclosure about a process for the production of acrylic acid by the oxidation of propylene.

U.S. Pat. No. 4,052,450 discloses a process which comprises subjecting an α-olefin to oxidation with molecular oxygen or to ammoxidation in the vapor-phase by the use of a catalyst containing small amounts of indium and/or aluminum and/or lanthanum and/or gallium in the form of oxides and/or mixed oxides and containing molybdenum and bismuth and optionally other elements in the form of oxides or mixed oxides at a temperature in the range of 280° to 450° C., when necessary, in the presence of steam and/or ammonia thereby producing a corresponding α, β-olefinically unsaturated aldehyde or nitrile. In this specification, there is a mention purporting that the content of the α-olefin such as propylene or isobutylene in the synthetic raw gas generally falls in the range of 0.5 to 15% by volume, particularly in the range of 2 to 6% by volume when oxygen is used in place of air, and in the range of 6 to 15% by volume when pure oxygen is used and part of the reaction off-gas remaining after removal of acrylic acid is added (by recycling) to the gaseous mixture subjected to the oxidation. The concentration of oxygen generally falls in the range of 2 to 20% by volume, preferably 5 to 15% by volume. The mixture further comprises carbon monoxide, carbon dioxide, and nitrogen and additionally contains, mostly in small amounts, rare gases, hydrogen, ethylene, and propane. The synthetic raw gas may contain steam. There is a mention purporting that the content of steam generally falls below 40% by volume, desirably below 20% by volume and particularly below 10% by volume, and particularly preferably in the range of 2 to 8% by volume. In this patent publication, however, no specific mention is made of production of acrylic acid by oxidation of propylene.

Japanese Patent Publication SHO 39(1964)-3,670 discloses a process which uses pure oxygen as an oxygen source, withdraws a circulation gas formed of unaltered propylene, replenishes the circulation gas with fresh supply of propylene, oxygen, and steam, returns the refreshed circulation gas to the reactor, and uses as a diluent gas the $CO_2$ and CO produced during the reaction and steam.

G.B. Patent No. 1,390,271 discloses a process which withdraws a carbonyl compound and a carboxylic acid compound while pure oxygen is used as an oxidizing agent, treats the produced mixture remaining after the withdrawal for removal of carbon dioxide, and circulates to the reactor the residual mixture containing unaltered olefin and oxygen in combination with water.

G.B. Patent No. 1,220,568 discloses use of pure oxygen as an oxidizing agent. As a diluent for propylene and oxygen, the off-gas from the second stage reaction and remaining after separation of acrylic acid is used. This diluent contains carbon oxides and steam as inactive components. According to the preferred embodiments cited in the specification, the oxygen:propylene ratio is substantially less than 1.5:1. Thus, this process has the possibility of disposing the catalyst to reduction due to insufficient supply of oxygen, lowering the selectivity of the reaction for acrolein and acrylic acid and the conversion of propylene and impairing the service life of the catalyst.

The improvement of the productivity of a process for the manufacture of acrylic acid, as described above, is achieved by increasing the amount of propylene to be supplied as a raw material and minimizing the load upon the catalyst by shortening the contact time of the raw gas on the catalyst bed to the fullest possible extent. An increase in the amount of propylene subjected to the reaction (with a simultaneous elevation of the space velocity) results in an increase in the volume of heat generated by the reaction of oxidation. An attempt at increasing the conversion of propylene entails an inevitable increase in the oxygen concentration of the raw gas. The increased oxygen concentration renders it difficult to prevent propylene from reaching a range of explosion. Heretofore, for the removal of a large volume of heat and the protection of the reaction system against the danger of explosion, the forced entrainment of steam by the raw gas and the dilution of the portion of the catalyst abundantly participating in the reaction with an inactive carrier, for example, have been resorted to an effective measures. The decrease of the oxygen concentration in the raw gas by the addition of the recovered off-gas has also been employed as an effective measure. These measures, however, necessitate extra labor for the dilution of the catalyst, entail an inevitable decrease in the concentration of the recovered acrylic acid due to the addition of steam, and induces loss of energy due to the separation of acrylic acid. The conventional processes have failed to effect sufficient removal of the heat of reaction from the off-gas and have attained a propylene oxidation with a high propylene throughput only to a limited extent.

An object of this invention, therefore, is to provide a novel process for the production of acrylic acid by the catalytic vapor-phase oxidation of propylene.

Another object of this invention is to provide a safety oxidation process with a high productivity, in which production of acrylic acid is in a high yield for a long period of time even under reaction conditions to impose a high load on a catalyst.

SUMMARY OF THE INVENTION

In the production of acrylic acid by the two-stage catalytic vapor-phase oxidation of propylene with molecular oxygen, the first stage for oxidizing propylene to produce mainly acrolein and the second stage for oxidizing acrolein to produce mainly acrylic acid, the objects described above are accomplished by a process which comprises supplying to the first-stage a raw gas containing a saturated aliphatic hydrocarbon having 1 to 5 carbon atoms in an amount in the range of 5 to 70% by volume, carbon dioxide in an amount in the range of 3 to 50% by volume, and the aliphatic hydrocarbon and the carbon dioxide in a total amount in the range of 20 to 80% by volume and further containing steam in an amount in the range of 0.5 to 8 mols per mol of propylene. It is advantageous in commercial operation that aforesaid raw gas is prepared by utilizing the off-gas for the first-stage reaction after recovery of object products. In this invention, the raw gas is prepared by utilizing more than 50% in volume of off-gas after recovery of mainly acrylic acid.

DESCRIPTION OF THE PREFERRED EMBODIMENTS

In the present invention, it has been found that the catalytic vapor-phase oxidation of propylene in the presence of molecular oxygen can be continued with a high efficiency for a long time even under reaction conditions apt to impose a heavy load upon the catalyst by using a diluent gas containing a saturated aliphatic hydrocarbon having 1 to 5 carbon atoms in an amount in the range of 5 to 70% by volume, carbon dioxide in an amount in the range of 3 to 50% by volume, and the aliphatic hydrocarbon and carbon dioxide in a total amount in the range of 20 to 80% by volume and further containing steam in an amount in the range of 0.5 to 8 mols per mol of propylene. It is advantageous in commercial operation that aforesaid raw gas is prepared by utilizing the off-gas for the first-stage reaction after recovery of object products. In this invention, the raw gas is prepared by utilizing more than 50% in volume of off-gas after recovery of mainly acrylic acid. This invention has been perfected as the result. As regards the mechanism responsible for the effect produced by the adoption of the reaction conditions contemplated by the present invention, the fact that the raw gas of the specific composition has a large thermal capacity as compared with steam, nitrogen, etc. heretofore used as a diluent and, therefore, has a great effect in the removal of the heat of reaction may be ascribed as one cause for the mechanism. The specific heat under constant pressure in the neighborhood of 300° C. (Kcal/Kgmol.deg.) is 12.5 for methane, 21.3 for ethane, 30.9 for propane, 40.3 for butane, 11.5 for carbon dioxide, 8.8 for steam, 7.8 for oxygen 7.3 for carbon monoxide, 7.1 for nitrogen, 5.0 for argon and 5.0 for air.

The beneficial points manifested in the execution of the present invention may be summarized as follows. Owing to an increase in the thermal capacity of the reaction gas itself, the gas itself is capable of absorbing the heat generated by the reaction of oxidation and the effect in the removal of the heat of the reaction is notably enhanced and, as the result, the otherwise possible increase in the heat of the catalyst bed itself is repressed and the thermal load exerted on the catalyst is mitigated to a great extent. Then, owing to the presence of carbon oxides in high concentrations in the raw gas for the reaction, the possibility of explosion of propylene is eliminated and the reaction of propylene in a high concentration at a high space velocity is rendered feasible and, as the result, the desire to heighten the productivity of the process is attained and the production of acrylic acid in a high concentration is realized and the consumption of energy for the separation and purification of acrylic acid is repressed. Further owing to the decrease of temperature difference ($\Delta T$) between the temperature of the catalyst bed and the reaction temperature (external heat transfer medium), the selectivity of the reaction for acrolein and/or acrylic acid is improved and the yield is consequently improved and the temperature difference ($\Delta T$) is further lowered and, as the result, the stability of the retention of the catalyst components in the catalyst is enhanced, the possible deterioration of the catalyst is diminished, and the service life of the catalyst is lengthened. Moreover, the adoption of this process permits use of the catalyst in a carried form. Generally, when a catalyst for the oxidation of propylene is used in a form coated to or deposited on an inert carrier, for example, it retains the activity intact in the early stage of service but, with elapse of time, tends to lose the activity abruptly. This sharp decline of the activity may be ascribable to the degeneration of the catalyst itself by the heat of reaction. Since the adoption of this process permits smooth removal of the heat of reaction, the temperature difference ($\Delta T$) is decreased and the thermal deterioration of the catalyst is curbed and, as the result, the use of the catalyst on a carrier is realized. Further, more, as the amount of recycling off-gas from the reactor except condensable components is more than 50% in volume, effective use of propylene is enhanced.

This process necessitates coexistence of steam with carbon dioxide in the first-stage reaction gas as an indispensable requirement. In one aspect, the steam is effective in promoting the process probably because it facilitates the desorption of the main products of the catalytic vapor-phase oxidation of propylene, i.e. acrolein and acrylic acid as another useful compound and particularly high boiling products as well or probably because it participates directly in the reaction. This effect is not attained by the presence of such coexisting gases as carbon dioxide and saturated hydrocarbon alone. If the steam contained at all has a concentration of not more than 0.5 mol per mol of propylene, it fails to manifest a conspicuous effect in facilitating the separation of secondary products of the reaction. As the result, the reaction temperature is suffered to rise quickly (and the service life of the catalyst is consequently shortened) so that the catalyst is prevented from fulfiling its function advantageously in the operation of the process on commercial scale. This effect of the steam upon the service life of the catalyst acts heavily on the catalyst for the oxidation of acrolein which is composed mainly of molybdenum oxide and vanadium oxide. Further the coexisting steam is effective in causing the carbon dioxide to be converted into an acidic gas through the agency of steam and, as the result, improving the selectivity of the reaction for conversion of propylene to acrolein. It is inferred for uncertain reasons that the acidic gas participates in controlling the acid base groups in the catalyst.

Conversely, if the steam is contained in an unduly large concentration, the production of an aqueous acrylic acid solution with a sufficiently high concentration is not attained. Moreover, when the steam is recycled through the reaction system in accordance with one aspect of the present invention, the unduly high steam concentration may possibly necessitate elevation of the temperature at the top of an acrylic acid collection column and entail inevitable circulation of a large volume of impurities through the reaction system.

As concerns the purity of the propylene to be used as raw material in the present invention, it may be decided with due consideration to the fact that the propane contained therein is highly effective in the removal of the heat of reaction because of its high thermal capacity. Preferably, the propylene purity is not more than 97% by volume (with propane accounting for the balance). For example, the propane-containing propylene which is obtained in the dehydrogenation of propane by oxidation can be used advantageously. If the propylene to be used has an unduly large propane content, there is a disadvantage that the amount of the off-gas to be used for the circulation decreases so much as to impair the effective utilization of unaltered propylene.

The catalyst to be used in this invention, for the purpose of the first-stage reaction, is desired to be an oxide catalyst containing Mo, Fe, and Bi. This catalyst is represented by the following general formula:

$$Mo_aW_bBi_cFe_dA_eB_fC_gD_hO_x$$

wherein Mo is molybdenum, Bi is bismuth, W is tungsten, Fe is iron, O is oxygen, A is at least one element selected from the group consisting of nickel and cobalt, B is at least one element selected from the group consisting of alkali metals, alkaline earth metals, and thallium, C is at least one element selected from the group consisting of phosphorus, arsenic, boron, and niobium, and D is at least one element selected from the group consisting of silicon, aluminium, and titanium, and the subscripts a, b, c, d, e, f, g, h, and x are respectively the numbers of atoms of the elements Mo, W, Bi, Fe, A, B, C, D, and 0, providing that a=2 to 10, b=0 to 10, on condition that a+b=12, c=0.1 to 10.0 d=0.1 to 10, e=2 to 20, f=0.005 to 3.0, g =0 to 4, h 0.5 to 15, and x is a number required to satisfy the valance requirements of the other elements.

The oxide catalyst for use in this invention may be in the form of pellets, beads, or rings containing a through hole which are produced by a tableting machine or an extruding machine. Otherwise, it may be used similarly effectively herein in a form having catalytic components deposited on a refractory carrier.

The catalyst for use in the second-stage reaction is desired to be an oxide catalyst containing molybdenum and vanadium, preferably an oxide catalyst represented by the following general formula:

$$Mo_mV_nQ_qR_rS_sT_tO_y$$

wherein Mo is molybdenum, V is vanadium, Q is at least one element selected from the group consisting of tungsten and niobium, R is at least one member selected from the group consisting of iron, copper, bismuth, chromium, and atimony, S is at least one element selected from the group consisting of alkali metals and alkaline earth metals, T is at least one element selected from the group consisting of silicon, aluminum and titanium, and 0 is oxygen and the subscripts m, n, q, r, s, t, and y are respectively the numbers of atoms of the corresponding elements, providing that n=2 to 14, q =0 to 12, r=0 to 6, s=0 to 6, t=0 to 30 where m=12, and y is a number determined by the valance requirements of the other elements in the oxidation states.

Of course, this oxide catalyst may be effectively used in a form having catalytic components deposited on a refractory carrier.

As concerns the reaction conditions, the reaction temperature in the first-stage reaction is in the range of 250° to 450° C., preferably 270° to 370° C. As regards the reaction gas composition, the content of propylene is in the range of 5 to 20% by volume, preferably 7 to 15% by volume, that of oxygen in the range of 8 to 40% by volume, preferably 12 to 30% by volume, that of a saturated aliphatic hydrocarbon having 1 to 5 carbon atoms, preferably 1 to 3 carbon atoms, in the range of 5 to 70% by volume, preferably 10 to 60% by volume, that of carbon dioxide in the range of 3 to 50% by volume, preferably 5 to 40 % by volume, (providing that the total content of the hydrocarbon and carbon dioxide is in the range of 20 to 80% by volume, preferably 30 to 70 % by volume), and that of steam in the range of 3 to 50% by volume, preferably 5 to 40% by volume, (providing that the molar ratio of steam to propylene is in the range of 0.5 to 8, preferably 0.6 to 5), the molar ratio of oxygen to propylene is in the range of 1.4 to 4.0, preferably 1.6 to 3.0, and the contact time is in the range of 1.0 to 7.2 seconds, preferably 1.8 to 6.0 seconds. The catalyst to be used must be capable of effecting conversion of propylene in a ratio of not less than 70 mol %, preferably not less than 80 mol %. As regards the conditions for the second-stage oxidation, the reaction temperature is in the range of 180° to 350° C., preferably 200° to 320° C., and the contact time is in the range of 1.0 to 7.2 seconds, preferably 1.6 to 6.0 seconds. The catalyst to be used in the second-stage reaction must be capable of producing acrylic acid from propylene through the whole two-stage operation in a per pass yield of not less than 70 mol %, preferably not less than 80 mol %.

Now, the present invention will be described more specifically below with reference to working examples and comparative examples. It should be noted, however, that this invention is not limited to these working examples. The terms "conversion," "per pass yield," and "recycle yield" as used herein are defined as follows.

$$\text{Conversion (\%) of propylene} = \frac{\text{Mols of propylene converted}}{\text{Mols of propylene supplied}} \times 100$$

$$\text{Per pass yield (\%) of acrylic acid} = \frac{\text{Mols of acrylic acid produced}}{\text{Mols of propylene supplied}} \times 100$$

$$\text{Recycle yield (\%) of acrylic acid} = \frac{\text{Mols of acrylic acid produced}}{\text{Mols propylene added for replenishment}} \times 100$$

EXAMPLE 1

Preparation of First-Stage Catalyst

In 15 liters of water kept heated, 10.62 kg of ammonium molybdate and 3.24 kg of ammonium paratungstate added thereto were vigorously stirred (to obtain Solution A).

Separately, 7.00 kg of cobalt nitrate was dissolved in 2 liters of water, 2.43 kg of ferric nitrate in 2 liters of water, and 2.92 kg of bismuth nitrate in 3 liters of water acidified in advance by addition of 0.6 liter of concentrated nitric acid. A mixture of the three nitrate solution obtained above was added dropwise to the Solution A mentioned above. Then, a solution obtained by dissolving 2.44 kg of silica sol containing silicon dioxide in a ratio of 20% by weight and 20.2 g of potassium hydroxide in 1.5 liters of water was added thereto, to give rise to a suspension. This suspension was evaporated by application of heat and subsequently molded and calcined in air at 450° C. for 6 hours, to produce a catalyst.

The composition of this catalyst in terms of the atomic ratio of component elements except for oxygen is expressed as follows:

$$Co_4Fe_1Bi_1W_2Mo_{12}Si_{1.35}K_{0.06}$$

Preparation of Second-Stage Catalyst

In 60 liters of water kept heated and stirred, 1.25 kg of ammonium paratungstate, 1.03 kg of ammonium metavanadate, 4.06 kg of ammonium molybdate, and 0.14 kg of ammonium dichromate were added and dissolved. Separately, 1.03 kg of copper nitrate was dissolved in 0.72 liter of water to produce an aqueous solution. These two solutions were mixed. In a stainless steel evaporator provided with a steam heater, the mixed solution and 12 liters of a granular carrier formed mainly of alpha-alumina particles (possessed of a surface area of not more than 1 m²/g, a porosity of 42%, and diameters in the range of 75 to 250 microns and containing pores such that the volume occupied by pores of diameters of 75 to 250 microns was 92% of the total volume of all the pores) added thereto were stirred, evaporated to dryness to effect deposition of the oxides of the mixed solution on the carrier. The composite thus obtained was calcined at 400° C. for five hours to produce a catalyst.

The composition of this catalyst in terms of the atomic ratio of component elements except for oxygen is expressed as follows:

$$Mo_{12}V_{4.6}Cu_{2.2}Cr_{0.6}W_{2.4}.$$

Reaction and Collection of Acrylic Acid

Twelve liters of the first-stage catalyst mentioned above was uniformly packed in a Multi tube reactor using 10 steel reaction tubes 25 mm in inside diameter and 3,000 mm in length and a shell adapted to effect exchange of heat by circulation of molten salt, and heated to 325° C.

Separately, in a tube reactor having 10 steel reaction tubes 25 mm in inside diameter and 3,000 mm in length and a shell adapted to effect exchange of heat by circulation of molten salt, 9.0 liters of the second-stage catalyst mentioned above was uniformly packed and heated to 260° C.

The two reactors were interconnected with a conduit provided with a heat-exchanger in such a manner that the reaction gas emanating from the reactor containing the first-stage catalyst was introduced into the reactor containing the second-stage catalyst. The produced gas emanating from the reactor containing the second-stage catalyst was introduced into an acrylic acid collection device comprising a stainless steel column 200 mm in inside diameter, a hot-water jacket formed on the outer wall of the column, 20 bubble caps spaced vertically inside the column, and a shell and tube type condenser disposed below the bubble caps thereby effecting collect on of acrylic acid in the form of an aqueous solution by causing the water containing a polymerization inhibitor (composed mainly of hydroquinone) to flow down the column from the top thereof and permitting discharge of the off-gas in a form containing steam in a concentration fixed by the column's top temperature. The steam-containing gas discharged from the acrylic acid collection device was returned in an uncondensed state, except for a small portion thereof which was purged, to the inlet of the reactor containing the first-stage catalyst, there to be replenished with fresh supply of propylene of purity of 95% (with the balance of propane) and oxygen of purity of 95.7% (with the balance mainly of argon), and introduced into the reactor containing the first-stage catalyst.

A mixed gas containing 7.0% by volume of propylene, 12.6% by volume of oxygen, 7.0% by volume of steam, 26.0% by volume of carbon dioxide, 13.0% by volume of carbon monoxide, 14.0% by volume of propane, and 20.4% by volume of argon was introduced at a rate of 16.2 m³/hr (on NTP basis) to the first-stage reactor. In this case, the yield of acrylic acid was highest when the conversion of propylene was 95.0%.

At this time, the recycling ratio of the off-gas to the first-stage reactor was 97.6%. As the result, the difference, ΔT, between the highest temperature of the catalyst bed in the first-stage reactor and the reaction temperature (the temperature of the molten salt as heat transfer medium) was 43° C. The yield of acrylic acid relative to the supplied propylene was 92.0% and the space time yield was 159.8 g of acrylic acid/hr.lit. of catalyst.

This reaction was continued over a period of 8,000 hours. At the end of this period, the salt bath temperature in the first-stage reaction was 330° C. and that in the second-stage reaction was 266° C. The conversion of propylene and the yield of acrylic acid were found to be respectively 95.0% and 91.7% stably.

COMPARATIVE EXAMPLE 1—1

The procedure of Example 1 was repeated, except that air was used as an oxygen source. In this case, the circulation ratio of the off-gas to the first-stage reactor was 0.

The first-stage inlet gas was composed of 7.0% by volume of propylene, 12.6% by volume of oxygen, 7.0% by volume of steam, and the balance of nitrogen plus small amounts of argon and propane. Steam was supplied as mixed amply in propylene as the raw material and with air. The highest yield of acrylic acid was obtained when the conversion of propylene was 95.5%. The molten salt temperature was 320° C. in the first-stage reaction and 260° C. in the last-stage reaction.

As the result, the temperature difference, $\Delta T$, was as large as 65° C. and the yield of acrylic acid relative to the supplied propylene was 84.5%. The space time yield was 146.8 g of acrylic acid/hr.lit. of catalyst. The unaltered propylene was wasted.

COMPARATIVE EXAMPLE 1—2

The procedure of Comparative example 1—1 was repeated, except that the first-stage inlet gas was composed of 7.0% by volume of propylene, 12.6% by volume of oxygene, 7.0% by volume of steam, 10.0% by volume of carbon dioxide, the balance of nitrogen plus small amounts of argon and propane.

As the result, the temperature difference, $\Delta T$, was as large as 63° C. and yet the yield of acrylic acid relative to the supplied propylene was 86.6 mol %. This improvement over the yield of Comparative example 1—1 was due to the addition of carbon dioxide. This effect was due more to the function of carbon dioxide as an acidic gas than to the larger thermal capacity of carbon dioxide than that of nitrogen.

COMPARATIVE EXAMPLE 1—3

The procedure of Example 1 was repeated, except that a mixed gas containing 7.0% by volume of propylene, 12.6% by volume of oxygen, 2.0% by volume of steam, 31.5% by volume of carbon dioxide, 19.7% by volume of carbon monoxide, 10.9% by volume of propane, and the balance of argon was introduced at a rate of 16.2 m3/hr (on NTP basis) to the first-stage reactor. The amount of steam was adjusted by the temperature of the off-gas at the outlet of the acrylic acid collection device, with the reaction temperature in the first-stage reactor regulated at 325° C. and that in the second-stage reactor at 260° C. At this time, the yield of acrylic acid was highest when the conversion of propylene was 94.0%.

During the reaction, the circulation ratio of the off-gas to first-stage reactor was 96.9%. As the result, the temperature difference, $\Delta T$, in the first-stage reactor was 45° C., the yield of acrylic acid relative to the supplied propylene was 85.7%, and the space time yield was 148.9 g of acrylic acid/hr. lit. of catalyst.

This reaction was continued over a period of 4,000 hours. At the end of this period, the salt bath temperature in the first-stage reaction was required to be raised to 335° C. and that in the second-stage reaction to 270° C. At this point, the conversion of propylene and the yield of acrylic acid were respectively 93.8% and 84.8%. The reaction was controlled with difficulty because the catalyst suffered heavy degradation of activity and the reaction conditions were always varied. This adverse situation may be logically explained by a supposition that the insufficient supply of steam obstructed easy separation of by-products from the surface of the catalyst and the reaction proceeded rather excessively so as to induce reduction of the catalyst.

COMPARATIVE EXAMPLE 2

The procedure of Example 1 was repeated, except that air was used as an oxygen source. The steam source at the inlet of the first-stage reactor was secured by the regulation of the temperature of the top of the acrylic acid collection device. The molten salt temperature was 320° C. and 260° C. respectively in the first-stage and second-stage reactors. At this time, the circulation ratio of the off-gas was 36.7%. The gas at the inlet of the first-stage reactor was composed of 0.57% by volume of carbon dioxide, 0.59% by volume of propane, 0.28% by volume of carbon monoxide, 0.9% by volume of argon, and the balance of nitrogen.

As the result, the temperature difference, $\Delta T$, was 64° C., the yield of recycled acrylic acid relative to the supplied propylene was 85.6%, and the space time yield was 148.7g of acrylic acid/hr. lit. of catalyst.

COMPARATIVE EXAMPLE 3

The procedure of Example 1 was repeated, except that an oxygen source containing 80.0% of oxygen and 20.0% of nitrogen was used in the place of the oxygen of purity of 95.7%. The gas supplied to the first-stage reaction was composed of 7.0% by volume of propylene, 12.6% by volume of oxygen, 14.0% by volume of carbon dioxide, 7.0% by volume of carbon monoxide, 7.0% by volume of steam, 0.6%. by volume of propane, and the balance of nitrogen. The reaction temperature at which the highest yield was obtained was 325° C. in the first-stage reaction and 265° C. in the second-stage reaction. At this time, the conversion of propylene was 95.0%.

As the result, the temperature difference, $\Delta T$, was 60° C., the circulation ratio of the off-gas was 94.2%, the yield of acrylic acid relative to the supplied propylene was 89.2%, and the space time yield was 155.0% of acrylic acid/hr. lit. of catalyst.

EXAMPLE 2

The procedure of Example 1 was repeated, except that the amount of first-stage catalyst was changed from 12 liters to 8.1 liters and that of the second-stage catalyst from 9 liters to 8.1 liters. The conversion of propylene at which the yield of acrylic acid was highest was 95%. At that time, the molten salt temperature was 330° C. and 270° C. respectively in the first-stage and second-stage reaction.

To the first-stage reaction, a mixed gas containing 11.0% by volume of propylene, 19.8% by volume of oxygen, 7.0 % by volume of steam, 22.5% by volume of carbon dioxide, 13.0% by volume of carbon monoxide, 11.0% by volume of propane, and the balance of argon was supplied at a rate of 16.2 m$^3$/hr. (on NTP basis).

As the result, the temperature difference, $\Delta T$, was 51° C., the recycle ratio of the off-gas was 95.1%, the yield of acrylic acid relative to the supplied propylene was 90.3%, and the space time yield was 319.5 g of acrylic acid/hr. lit. of catalyst.

EXAMPLE 3

Preparation of First-Stage Catalyst

A catalyst of an elementary composition, $Co_4Bi_1Fe_1W_2Mo_{10}Si_{1.35}Tl_{0.04}Ba_{0.05}$ except for oxygen, was prepared by following the procedure of Example 1, except that thallium nitrate and barium nitrate were used in the place of potassium hydroxide.

Preparation of Second-Stage Catalyst

In 60 liters of water kept heated and stirred, 897 g of ammonium metavanadate, 4,060 g of ammonium molybdate and 575 g of silica sol which contains 20% in weight silicon dioxide were solved, and a solution of 926 g of copper nitrate and 155 g of ferric nitrate in 3.8 liters of water were mixed in it. In a stainless steel evaporator provided with a steam heater, the mixed solution obtained as described above and 12 liters of the same granular carrier as used in Example 1 as a carrier base were stirred and evaporated to dryness to effect deposition of the catalystic components on the carrier, and then calcined at 400° C. for six hours to complete a catalyst. The composition of this catalyst in terms of the atomic ratio of component elements except for oxygen is expressed as follows:

$$Mo_{12}V_3Cu_2Fe_{0.2}Si_{1.0}$$

The reaction and the collection of the produced acrylic acid were carried out by following the procedure of Example 2. The results are shown in Table 1. The reaction temperature was fixed at a level at which the yield of acrylic acid was highest.

EXAMPLE 4

Preparation of First-Stage Catalyst

A catalyst of an elementary composition, $Co_4Bi_1Fe_1W_2Mo_{10}Si_{1.35}Cs_{0.02}Ti_{1.0}$ except for oxygen, was obtained by following the procedure of Example 1, except that cesium nitrate was added in place of potassium hydroxide and titanium dioxide was added simultaneously with 20% by weight of silica sol.

Preparation of Second-Stage Catalyst

In 75 liters of water, 10.00 kg of ammonium molybdate was dissolved by heating. To this solution, 1.38 kg of ammonium metavanadate, 7.06 kg of niobium hydroxide, 1.02 kg of ferrous oxalate, 0.56 kg of cuprous chloride, and 0.28 kg of potassium nitrate were sequentially added while under ample stirring. The mixture resulting from the heating and stirring and 4.25 kg of $SiO_2$ powder added thereto were evaporated to dryness and then pulverized, molded in the form of tablets measuring 6.0 mm in outside diameter and 6.6 mm in length and containing a through hole 2.0 mm in diameter, and calcined at 420° C. for five hours. The composition of this catalyst in terms of atomic ratio of component elements except for oxygen is expressed as follows:

$$Mo_{12}V_{2.5}Nb_{8.4}Cu_{1.2}Fe_{1.2}K_{0.6}Si_{15}$$

The reaction and the collection of the produced acrylic acid were carried out by following the procedure of Example 2. The results are shown in Table 1.

EXAMPLE 5

Preparation of First-Stage Catalyst

A catalyst oxide of an elementary composition, $Co_4Bi_1Fe_1Mo_{10}W_2Si_{1.35}Sr_{0.06}$ except for oxygen, was prepared by following the procedure of Example 1, except that strontium nitrate was used in place of potassium hydroxide. It was molded in the form of rings measuring 6.0 mm in outside diameter and 6.6 mm in length and containing a through hole 2.00 mm in diameter, to produce rings of catalyst.

Preparation of Second-Stage Catalyst

A catalyst of an elementary composition, $Mo_{12}V_{4.0}Sb_{0.5}Mg_{2.0}Al_{5.0}$ except for oxygen, was prepared by following the procedure of Example 1, except that antimony pentoxide as an antimony source, magnesium nitrate as a magnesium source, and aluminum oxide as an aluminum source were used in place of ammonium paratungstate, ammonium dichromate, and copper nitrate.

The reaction and the collection of the produced acrylic acid were carried out by following the procedure of Example 2. The results are shown in Table 1.

EXAMPLE 6

Preparation of First-Stage Catalyst

A catalytic oxide of an elementary composition, $Co_4Bi_1Fe_1Mo_{10}W_2Si_{1.35}Ca_{0.06}N_{0.5}$ except for oxygen, was prepared by following the procedure of Example 1, except that calcium nitrate was used in place of potassium hydroxide and niobium pentoxide as added after the addition of silica sol and calcium nitrate. This catalytic oxide was molded in the form of rings measuring 6.0 mm in outside diameter and 6.6 mm in length and containing a through hole 2.0 mm in diameter, to produce rings of catalyst.

Preparation of Second-Stage Catalyst

In 75 liters of water kept heated and stirred, a mixed solution containing 2.54 kg of ammonium paratungstate, 2.21 kg of ammonium metavanadate, and 10.00 kg of ammonium molybdate and an aqueous solution obtained by dissolving 2.68 kg of strontium nitrate and 2.28 kg of copper nitrate in 13 liters of water were mixed. The resultant mixed solution and 0.38 kg of titanium dioxide powder added thereto were evaporated to dryness, pulverized, molded in the form of rings measuring 6.0 mm in outside diameter and 6.6 mm in length and containing a through hole 2.0 mm in diameter, and calcined at 400° C. for five hours. The composition of the resultant catalytic oxide in terms of atomic ratio of component elements except for oxygen is expressed as follows:

$$Mo_{12}V_4W_2Cu_2Sr_2Ti_1$$

The reaction and the collection of the produced acrylic acid were carried out by following the procedure of Example 2. The results are shown in Table 1.

EXAMPLE 7

Preparation of First-Stage Catalyst

A catalytic oxide of an elementary composition, $Co_3Ni_1Bi_1Fe_2Mo_{12}Si_{4.7}P_1Rb_{0.1}$, was prepared by following the procedure of Example 5, except that nickel nitrate was added simultaneously with cobalt nitrate, rubidium nitrate was used in place of potassium nitrate, and phosphoric acid was used in place of ammonium paratungstate. The catalytic oxide was molded in the form of rings measuring 6.0 mm in outside diameter and 6.6 mm in length and containing a through hole 2.0 mm in diameter and calcined in air at 500° C. for six hours.

Preparation of Second-Stage Catalyst

A catalystic oxide of an elementary composition, $Mo_{12}V_6W_4Cu_1Fe_1Na_{0.5}Al_5$, was prepared by following the procedure of Example 6, except that ferric nitrate as an iron source, sodium nitrate as a sodium source, and aluminum oxide as an aluminum source were used in place of strontium nitrate and titanium dioxide. This catalytic oxide was molded in the form of rings measuring 6.0 mm in outside diameter and 6.6 mm in length and containing a through hole 2.0 mm in diameter and calcined at 400° C. for five hours.

The reaction and the collection of the produced acrylic acid were carried out by following the procedure of Example 2. The results are shown in Table 1.

EXAMPLE 8

Preparation of First-Stage Catalyst

A catalytic oxide of an elementary composition, $Mo_{12}Bi_1Fe_2Ni_1Co_3Si_{4.7}B_{2.0}K_{0.2}Al_{1.0}$ except for oxygen, was prepared by following the procedure of Example 5, except that nickel nitrate and aluminum nitrate were added simultaneously with cobalt nitrate and potassium nitrate was used in place of ammonium paratungstate and boric acid was used in place of strontium nitrate. This catalytic oxide was molded in the form of rings measuring 6.0 mm in outside diameter and 6.6 mm in length and containing a through hole 2.0 mm in diameter and calcined in air at 500° C. for six hours.

Preparation of Last-Stage Catalyst

A catalyst oxide of an elementary composition, $Mo_{12}V_8W_4Cu_{1.0}Bi_{0.05}Rb_{0.05}Si_{5.0}$ was prepared by following the procedure of Example 7, except that bismuth nitrate was used in place of ferric nitrate, rubidium nitrate in the place of sodium nitrate, and silicon oxide in the place of aluminum oxide. This catalytic oxide was molded in the form of rings measuring 6.0 mm in outside diameter and 6.6 mm in length and containing a through hole 2.0 mm in diameter and calcined at 400° C. for five hours.

The reaction and the collection of the produced acrylic acid were carried out by following the procedure of Example 2. The results are shown in Table 1.

EXAMPLE 9

Preparation of First-Stage Catalyst

A catalytic oxide of an elementary composition, $Co_3Ni_1Bi_1Fe_2Mo_{12}Si_{4.7}As_{0.5}Tl_{0.05}$ except for oxygen, was prepared by following the procedure of Example 7, except that arsenious acid was used in place of phosphoric acid and thallium nitrate in place of rubidium nitrate. This catalytic oxide was molded in the form of rings measuring 6.0 mm in outside diameter and 6.6 mm in length and containing a through hole 2.0 mm in diameter and calcined under a current of air at 500° C. for six hours.

Preparation of Second-Stage Catalyst

A catalytic oxide of an elementary composition, $Mo_{12}V_8W_1Bi_1Cs_{0.05}Si_5$ except for oxygen, was prepared by following the procedure of Example 6, except that bismuth nitrate was used in place of copper nitrate and cesium nitrate in place of stronitum nitrate and silicon dioxide was used in place of titanium dioxide.

The reaction and the collection of the produced acrylic acid were carried out by following the procedure of Example 2. The results are shown in Table 1.

EXAMPLE 10

In a single reaction vessel adapted to permit selective control of reaction temperatures in two separate internal sections thereof and ensure avoidance of a range of inflammability of propylene or acrolein instead of a system using two reactors, one for the first-stage reaction and the other for the second-stage reaction, and having a demister attached as flame arrester on the inlet side of the first-stage reactor and a packing material placed to fill up an empty space intervening between the demister and the inlet side of the first-stage reactor to reduce the space density, a reaction was carried out under the following conditions.

Preparation of First-Stage Catalyst and Second-Stage Catalyst

The same catalysts as produced in Example 1 were prepared.

Methods for Reaction and Collection of Acrylic Acid

A reaction was carried out by following the procedure of Example 2, except that the conversion of propylene was fixed at 95.0% to maximize the yield of acrylic acid and the molten salt temperature was fixed at 335° C. and 275° C. respectively in the first-stage and the second-stage. To the first-stage reactor, a mixed gas containing 15% by volume of propylene, 27.0% by volume of oxygen, 10% by volume of steam, 17.7% by volume of carbon dioxide, 10.1% by volume of carbon monoxide, 8.4% by volume of propane, and the balance of argon was introduced at a rate of 16.2 m³/hr (on NTP basis). The results are shown in Table 1.

EXAMPLE 11

A reaction was carried out by following the procedure of Example 1, except that a mixture containing 55.0% by volume of propylene and 45.0% by volume of propane was used as a raw material for propylene. To the first-stage reactor, a mixed gas containing 7.0% by volume of propylene, 12.6% by volume of oxygen, 7.0% by volume of steam, 58.8 % by volume of propane, 5.2% by volume of carbon dioxide, 3.6% by volume of carbon monoxide, and the balance of argon was introduced at a rate of 16.2 m³/hr (on NTP basis). The yield of acrylic acid was highest when the conversion of propylene was 95.0%. The results are shown in Table 1.

EXAMPLE 12

A reaction was carried out by following the procedure of Example 10, except that a mixture containing 55% by volume of propylene and 45% by volume of propane was used as a raw material for propylene. A mixed gas containing 15.0% by volume of propylene, 27.0% by volume of oxygen, 10.0% by volume of steam, 37.4% by volume of propane, 5.2% by volume of carbon dioxide, 3.0% by volume of carbon monoxide, and the balance of argon was introduced at a rate of 16.2 m³/hr (on NTP basis) into the first-stage reactor. The yield of acrylic acid was highest when the conversion of propylene was 95%. The results are shown in Table 1.

TABLE 1

| Ex. | Gas composition at inlet of first-stage reactor (% by volume) | | | | | | | | SV(Hr$^{-1}$) | | Reaction temperature (°C.) | |
|---|---|---|---|---|---|---|---|---|---|---|---|---|
| | propylene | Oxygen | Steam | Propane | Carbon dioxide | Carbon monooxide | Argon | Nitrogen | SV$_1$ | SV$_2$ | T$_1$ | T$_2$ |
| 3 | 11 | 19.8 | 7 | 9.3 | 22.0 | 17.6 | 13.0 | — | 2000 | 2000 | 330 | 270 |
| 4 | 11 | 19.8 | 7 | 8.9 | 22.7 | 17.8 | 12.8 | — | 2000 | 2000 | 330 | 270 |
| 5 | 11 | 19.8 | 7 | 8.9 | 22.9 | 17.6 | 12.8 | — | 2000 | 2000 | 330 | 270 |
| 6 | 11 | 19.8 | 7 | 11.6 | 24.0 | 10.3 | 16.2 | — | 2000 | 2000 | 330 | 270 |
| 7 | 11 | 19.8 | 7 | 10.3 | 24.9 | 12.4 | 14.6 | — | 2000 | 2000 | 330 | 270 |
| 8 | 11 | 19.8 | 7 | 8.8 | 24.1 | 16.6 | 12.6 | — | 2000 | 2000 | 330 | 270 |
| 9 | 11 | 19.8 | 7 | 8.3 | 24.6 | 17.2 | 12.1 | — | 2000 | 2000 | 330 | 270 |
| 10 | 15 | 27 | 10 | 8.4 | 17.7 | 10.1 | 11.8 | — | 2000 | 2000 | 335 | 275 |
| 11 | 7 | 12.6 | 7 | 58.3 | 5.2 | 3.2 | 5.2 | — | 1350 | 1800 | 320 | 260 |
| 12 | 15 | 27 | 10 | 37.4 | 5.2 | 3.0 | 2.4 | — | 2000 | 2000 | 335 | 275 |

| Ex. | ΔT (°C.) | Conversion of propylene | Cycle yield of acrylic acid relative to supplied propylene | Space time yield (g of acrylic acid/hr. lit. of catalyst) |
|---|---|---|---|---|
| 3 | 53 | 96.3 | 88.0 | 311 |
| 4 | 52 | 94.5 | 87.1 | 308 |
| 5 | 53 | 94.8 | 88.4 | 313 |
| 6 | 50 | 95.9 | 90.9 | 322 |
| 7 | 51 | 94.3 | 89.8 | 318 |
| 8 | 54 | 93.4 | 87.2 | 309 |
| 9 | 56 | 96.0 | 86.0 | 304 |
| 10 | 60 | 95.0 | 89.6 | 432 |
| 11 | 40 | 95.0 | 91.6 | 159 |
| 12 | 55 | 95.0 | 88.6 | 428 |

SV$_1$, SV$_2$: Space velocities (hr$^{-1}$) of reaction gas in the second-stage and last-stage reactions.
T$_1$, T$_2$: Reaction temperatures in the second-stage and last-stage reactions.
ΔT; Difference between the reaction temperature and highest temperature of the catalyst bed in the first-stage reaction.

EXAMPLE 13

A first-stage catalyst similar to that of Example 1 was prepared as follows.

In 15 liters of water kept heated, 10.62 kg of ammonium molybdate and 3.24 kg of ammonium partungstate were stirred vigorously (to produce Solution A).

Separately, 7.00 kg of cobalt nitrate was dissolved in 2 liters of water, 2.43 kg of ferric nitrate in 2 liters of water and 2.92 kg of bismuth nitrate in 3 liters of water acidified in advance by addition of 0.60 liter of concentrated nitric acid. A mixture obtained by combining the three aqueous solutions was added dropwise to the Solution A mentioned above. To the resultant solution, 2.44 kg of silica sol containing 20% by weight of silicon dioxide and a solution of 20.2 g of potassium hydroxide in 1.5 liters of water were added. The resultant suspension was evaporated by heating and then dried in a drier air for 16 hours. Thereafter, the solid consequently produced was pulverized into a powder having a particle size of about 100 mesh. In a rotary pelletizer, 2.4 kg of this powder and an inert carrier of silica-alumina in the form of particles 3 to 5 mm in diameter were treated to effect deposition of catalytic components on the inert carrier. In this treatment, distilled water was used as a binder. The solid composite consequently obtained was dried in a drier at 120° C. for 12 hours and calcined at 450° C. for 6 hours in air to produce a catalyst.

A reaction was carried out by following the procedure of Example 1, except tat the molten salt temperature for the fist-stage catalyst (the temperature of the molten salt circulated inside the reactor shell) was fixed at 330° C. instead. As the result, the difference ΔT, between the highest temperature of the catalyst bed in the first-stage reactor and the reaction temperature was 38° C. The molten salt temperature 330° C. for the first-stage catalyst was the particular level at which the yield of acrylic acid reached the maximum. At that time, the conversion of propylene was 95.7% and the yield of acrylic acid was 91.3%.

This reaction was carried out over a period of 8,000 hours. At the end of this period, the salt bath temperature in the first-stage reaction as 343° C. and that in the second-stage reaction was 266° C. At that point, the conversion of propylene was 93.1% and the yield of acrylic acid was 88.8 mol %.

COMPARATIVE EXAMPLE 4

A reaction was carried out by following the procedure of Comparative example 1—1, except that the same first-stage catalyst as used in Example 13 (the catalyst having catalyst components deposited on an inert carrier with a rotary pelletizer) was used. As the result, the temperature difference, ΔT, was 58° C., the conversion of propylene 95.3%, and the yield of acrylic acid 86.0 mol %.

This reaction was continued over period of 4,000 hours. At the end of this period, the salt bath temperature in the first-stage was 355° C. and that in the second-stage reaction 264° C. At that point the conversion of propylene was 90.6% and the yield of acrylic acid 81.8%. These results clearly indicate that the first-stage catalyst suffered from a conspicuous degradation of activity in the reaction carried out by the conventional method.

EXAMPLE 14

A reaction was carried out by following the procedure of Example 1, except that a mixed gas containing 7.0% by volume of propylene, 12.6% by volume of oxygen, 35.0% by volume of steam, 16.8% by volume of carbon dioxide, 5.6% by volume of carbon monoxide, 9.3% by volume of propane, and the balance of argon was introduced at a rate 16.2 m$^3$/hr (on NTP basis) into the first-stage reactor. In this reaction, the amount of steam was regulated by the temperature of the off-gas at the top outlet of the acrylic acid collection device, with the reaction temperature in the first-stage reactor fixed at 325° C. and that in the second-stage reactor fixed at 260° C. At that point, the conversion of propylene was 94.5% and the yield of acrylic acid reached the maximum.

Then, the circulation ratio of the off-gas to the first-stage was 96.4%. As the result, the temperature difference, ΔT, in the first-stage reactor was 46° C. The yield of acrylic acid relative to the supplied propylene was 91.9% and the space time yield was 159.6 g of acrylic acid/hr.lit. of catalyst.

What is claimed is:

1. A process for the production of acrylic acid by the two-stage catalystic vapor-phase oxidation of propylene with molecular oxygen, the first stage for oxidizing propylene to produce mainly acrolein, the second stage for oxidizing acrolein to produce mainly acrylic acid and an off-gas obtained by separating acrylic acid from a mixed reaction gas produced by the second-stage reaction, which process comprises supplying to the first-stage reaction a raw gas containing more than 50% in volume of the off-gas and containing a saturated aliphatic hydrocarbon having 1 to 5 carbon atoms in an amount in the range of 5 to 70% by volume, carbon dioxide in an amount in the range of 3 to 50% by volume, said aliphatic hydrocarbon and said carbon dioxide in a total amount in the range of 20 to 80% by volume and further containing steam in an amount in the range of 0.5 to 8 mols per mol of propylene, and said molecular oxygen being supplied as a molecular oxygen-containing gas having purity of at least 90% by volume.

2. A process according to claim 1, wherein the concentration of propylene in said raw gas supplied to the first-stage reaction is in the range of 5 to 20% by volume and the concentration of molecular oxygen therein is in the range of 1.4 to 4.0 mols per mol of propylene.

3. A process according to claim 1, wherein the conversion of propylene in the first-stage reaction is at least 70%.

4. A process according to claim 1, wherein said saturated aliphatic hydrocarbon is at least one member selected from the group consisting of methane, ethane, and propane.

5. A process according to claim 1, wherein the steam to be supplied to the first-stage reaction is the steam contained in the off-gas obtained by separating acrylic acid from the mixed reaction gas produced by the second-stage reaction.

6. A process according to claim 1, wherein the molar ratio of oxygen to propylene is in the range of 1.4 to 4.0.

7. A process according to claim 6, wherein the amount of steam is in the range of 0.6 to 5 mols per mol of propylene.

8. A process according to claim 6, wherein the reaction temperature in the first stage is in the range of 250° C. to 450° C. and that in the second stage in the range of 180° C. to 350° C.

9. A process according to claim 1, wherein the reaction in the first stage is carried out in the presence of an oxide catalyst containing molybdenum, bismuth, and iron and the reaction in the second stage in the presence of an oxide catalyst containing molybdenum and vanadium.

* * * * *

UNITED STATES PATENT AND TRADEMARK OFFICE
CERTIFICATE OF CORRECTION

PATENT NO. : 5,218,146

DATED : June 8, 1993

INVENTOR(S) : Masahiro TAKATA et al

It is certified that error appears in the above-identified patent and that said Letters Patent is hereby corrected as shown below:

Title Page:

In Section [75], add -- Masamitsu Sasaki, Himeji --.

Signed and Sealed this

Eleventh Day of January, 1994

*Attest:*

BRUCE LEHMAN

*Attesting Officer*    *Commissioner of Patents and Trademarks*